(12) United States Patent
Arcilla et al.

(10) Patent No.: US 9,867,960 B2
(45) Date of Patent: Jan. 16, 2018

(54) COMPACT HUMIDIFIER

(71) Applicant: KONINKLIJKE PHILIPS N.V., Eindhoven (NL)

(72) Inventors: Mabini Arcilla, San Diego, CA (US); Smita Garde, Irvine, CA (US)

(73) Assignee: Koninklijke Philips N.V., Eindhoven (NL)

(*) Notice: Subject to any disclaimer, the term of this patent is extended or adjusted under 35 U.S.C. 154(b) by 367 days.

(21) Appl. No.: 14/410,421

(22) PCT Filed: Jul. 3, 2013

(86) PCT No.: PCT/IB2013/055439
§ 371 (c)(1),
(2) Date: Dec. 22, 2014

(87) PCT Pub. No.: WO2014/006574
PCT Pub. Date: Jan. 9, 2014

(65) Prior Publication Data
US 2015/0328431 A1    Nov. 19, 2015

Related U.S. Application Data

(60) Provisional application No. 61/667,554, filed on Jul. 3, 2012.

(51) Int. Cl.
*A61M 11/00* (2006.01)
*A61M 16/16* (2006.01)
(Continued)

(52) U.S. Cl.
CPC ........ *A61M 16/16* (2013.01); *A61M 16/0003* (2014.02); *A61M 16/0057* (2013.01);
(Continued)

(58) Field of Classification Search
CPC ...... A61M 16/1045; A61M 16/1075–16/1095; A61M 16/147; A61M 16/18–16/186; A61M 16/16; A61M 16/0003; A61M 16/0057; A61M 16/0875; A61M 16/109; A61M 16/0816; A61M 16/142; A61M 2205/3368; A61M 2205/3653;
(Continued)

(56) References Cited

U.S. PATENT DOCUMENTS 4,155,961 A    5/1979  Benthin
4,532,088 A    7/1985  Miller
(Continued)

FOREIGN PATENT DOCUMENTS

EP    0521726 A1    1/1993
EP    1281413 A2    2/2003
(Continued)

*Primary Examiner* — Steven Douglas

(57) ABSTRACT

A humidifier can be integrated with a ventilator allowing it to continue humidification during patient transport. The humidifier can be placed at the ventilator outlet port and have a size that adds minimal resistance and compliance in the inspiratory arm of the patient circuit. The innermost core of the humidifier is the heater element that is positioned inside a hydrophobic membrane, allowing for humidification of the gas flowing around the hydrophobic membrane.

13 Claims, 4 Drawing Sheets

(51) Int. Cl.
*A61M 16/00* (2006.01)
*A61M 16/08* (2006.01)
*A61M 16/10* (2006.01)
*A61M 16/14* (2006.01)

(52) U.S. Cl.
CPC .... *A61M 16/0816* (2013.01); *A61M 16/0875* (2013.01); *A61M 16/109* (2014.02); *A61M 16/142* (2014.02); *A61M 2205/3368* (2013.01); *A61M 2205/3653* (2013.01); *A61M 2205/7536* (2013.01)

(58) Field of Classification Search
CPC ........... A61M 2205/7536; B01D 63/06; B01D 2313/08; B01D 2313/10; B01D 2313/105; B01D 2313/26; B01D 2313/32; F24F 2003/1435
USPC .................................. 261/142, 101, DIG. 65
See application file for complete search history.

(56) References Cited

U.S. PATENT DOCUMENTS

| | | | |
|---|---|---|---|
| 4,943,704 A * | 7/1990 | Rabenau | A61M 16/16 261/104 |
| 5,062,145 A | 10/1991 | Zwaan et al. | |
| 5,367,604 A | 11/1994 | Murray | |
| 6,363,930 B1 | 4/2002 | Clawson et al. | |
| 6,367,472 B1 | 4/2002 | Koch | |
| 6,510,848 B1 | 1/2003 | Gibertoni | |
| 7,172,696 B1 * | 2/2007 | Martinez | B01D 53/22 210/321.8 |
| 7,476,212 B2 * | 1/2009 | Spearman | A61M 13/003 604/23 |
| 2003/0127095 A1 | 7/2003 | Gibertoni | |
| 2003/0192953 A1 | 10/2003 | Nitta | |
| 2006/0012057 A1 * | 1/2006 | Anthony | A61M 16/1075 261/154 |
| 2008/0127976 A1 * | 6/2008 | Acker | A61M 16/08 128/204.18 |
| 2008/0237902 A1 * | 10/2008 | Nagumo | B01D 53/22 261/104 |
| 2009/0056714 A1 * | 3/2009 | Cortez, Jr. | A61M 16/08 128/203.26 |
| 2010/0206308 A1 | 8/2010 | Klasek et al. | |

FOREIGN PATENT DOCUMENTS

| | | |
|---|---|---|
| WO | 03099367 A2 | 12/2003 |
| WO | 2012077052 A1 | 6/2012 |

* cited by examiner

COMPACT HUMIDIFIER

CROSS-REFERENCE TO PRIOR APPLICATIONS

This application is the U.S. National Phase application under 35 U.S.C. §371 of International Application No. PCT/IB2013/055439, filed on Jul. 3, 2013, which claims the benefit of U.S. Provisional Patent Application No. 61/667,554, filed on Jul. 3, 2012. These applications are hereby incorporated by reference herein.

FIELD OF THE INVENTION

The present invention relates to disposable active respiration humidifier for invasive or non-invasive ventilation of a patient.

BACKGROUND OF THE INVENTION

Respiration humidifiers are used to humidify the inspiratory gas of respirators to physiological levels.

The upper airway of a patient normally warms and humidifies the inspired gases during normal breathing. However, this is compromised when inspired gas is delivered by invasive or non-invasive ventilator. During invasive ventilation, the use of endotracheal tube bypasses the upper airway and so upper airways cannot contribute to heating and humidification of the delivered gases. This may lead to bronchial inflammation and related respiratory complications. During non-invasive ventilation, the nasal mucosa may not be able to adequately warm and humidify the inspired gas and can lead to thick mucus leading to increase in airway resistance and reduced lung compliance.

Hence in clinical practice, humidifiers are used to provide adequate heat and humidification to the delivered gas.

Generally humidifiers are rather bulky, heavy and may be characterized by a high degree of heat loss.

Humidifiers, such as heat and moisture exchangers (HME), also referred to as passive humidifiers may not be able to reliably maintain the temperature and humidity for high flow of inspired gas as humidity is usually maintained by the exhaled air. In contrast, heated humidifiers (HH), also referred to as active humidifiers try to maintain the temperature and humidity of delivered gas by controlling a heating plate that heats and evaporates the water in path of gas flow. However, these humidifiers introduce additional dead space or additional resistance in the circuit, or may have to be changed daily as for HMEs to avoid bacterial contamination, or cannot reliably deliver heated and humidified gas.

Such devices, which operate according to various principles, are arranged, in general, separated from the respirator.

One drawback of the separate arrangement for the user is, among other things, the large number of different tubing and connections.

Another drawback of the current humidifiers is that, during the transport of the patient, they need to be switched off and disconnected and thus switched to passive humidification.

Hence, an improved humidifier would be advantageous, and in particular a humidifier for use in a patient ventilation circuit, which can be integrated within a respirator, would be advantageous.

Furthermore, efficient humidifier would be advantageous, and in particular a humidifier for use in a patient ventilation circuit, which can continue active humidification during the transport of the patient, would be advantageous.

A low cost, lightweight humidifier would also be advantageous, and in particular a humidifier for use in a patient ventilation circuit, which has a fast response rate, would be advantageous.

An improved humidifier would also be advantageous, and in particular a more efficient and compact humidifier for use in a patient ventilation circuit would be advantageous.

OBJECT OF THE INVENTION

It is an object of the present invention to provide a humidifier that can be integrated with the ventilator allowing it to continue humidification during transport of a patient.

It is a further object of the invention to provide a humidifier that is compact, lightweight and low cost.

It is a further object of the present invention to provide an alternative to the prior art.

In particular, it may be seen as an object of the present invention to provide a humidifier that solves the above mentioned problems of the prior art by being placed in the inspiratory limb of the patient circuit.

SUMMARY OF THE INVENTION

Thus, the above described object and several other objects are intended to be obtained in a first aspect of the invention by providing a humidifier for use in a patient ventilation circuit, the humidifier comprising: a heater for heating a liquid; a hydrophobic membrane permeable to the vapour phase of the liquid, wherein the heater for heating the liquid is surrounded by the hydrophobic membrane permeable to the vapour phase of the liquid, thereby allowing for crossing of the membrane only by the vapour phase of the liquid.

The humidifier of the invention delivers optimally heated and humidified gas to the patient without the need to special heated-wire patient circuits.

Further the humidifier of the invention is compact and lightweight and adds minimal compliance, resistance and dead-space in the patient circuit.

In particular the characterizing position of the heater inside the hydrophobic membrane minimizes the heat loss and therefore improves the power efficiency of the humidifier.

In use, the heater heats the liquid producing vapours that can cross the hydrophobic membrane, as the membrane is permeable to vapour, while the liquid phase is blocked by the membrane.

The heater may include any means for heating a liquid, e.g. an ohmic resistance.

The hydrophobic membrane does not allow water, to cross the membrane. However, it is vapour permeable, thus allowing the vapour phase of the liquid to cross the membrane. The membrane surrounds the liquid and the heater, i.e. the heater and liquid are located inside the membrane.

Materials that can be used in the hydrophobic membrane may be polymer such as poly fluoro ethylene (PFE).

Generally, the liquid may be an aqueous solution, water based liquid or pure water.

In some other embodiments the humidifier further comprises a liquid chamber for containing the liquid.

The liquid is provided to the chamber through a supply line connected to an external water circuit or also simply to water canisters, bags or bottles. This has the advantage of allowing for use of the humidifier also during transportation of the patient.

In some other embodiments the humidifier further comprises a temperature sensor for sensing the temperature of the heater.

The temperature sensor may also be able to sense the temperature of the water, in the water chamber. The temperature sensor may also be able to sense the temperature of the air flowing outside the humidifier. These temperatures may be sensed by a single temperature sensor or by more than one sensor.

In some embodiments the temperature sensor is a thermocouple. The thermocouple may be located in between the heater and the liquid chamber sensing the difference in temperature between the liquid chamber and the heater.

In some further embodiments the heater for heating a liquid is comprised in a body and the hydrophobic membrane permeable to the vapour phase of the liquid is located onto an external surface of a housing for the body.

The housing may comprise a liquid chamber. The liquid chamber is a volume suitable for containing liquid to be heated by the heater and located between the hydrophobic membrane and the body, i.e. surrounding the body.

The liquid is supplied to the humidifier through a liquid channel comprised in the body. The fluid enters the liquid channel at the liquid supply inlet and flows towards the outlet, while is heated by the heater. The outlet of the liquid channel corresponds to the inlet of the liquid chamber comprised in the housing, where the liquid is further heated by the heater.

When in use the body is inserted into the housing so that the body is surrounded by the hydrophobic membrane and the vapour produced by heating the liquid, such as water, present in the liquid channel and liquid chamber can be released through the hydrophobic membrane.

In some embodiments the liquid chamber is comprised in the body.

In some other embodiments the liquid channel is not comprised in the body.

In some further embodiments the temperature sensor is comprised in the body.

The body may be made of metal, such as aluminium or aluminium alloys. Thus, the body may be a compact metal block where chambers for accommodating the different elements of the humidifier, such as the heater, the temperature sensor and the liquid channel, have been extruded.

Thus in a second aspect of the invention a humidifier for use in a patient ventilation circuit is provided, comprising: a body comprising a liquid supply channel, a temperature sensor chamber and a heater chamber; a housing for the body, configured to contain the body, the housing comprising a hydrophobic vapour permeable membrane substantially surrounding the body and located onto at least an external surface of the housing.

The body may comprise a heater inside the heater chamber and a temperature sensor inside the temperature sensor chamber. When in use the heater and the temperature sensor are connected via wiring to a control unit and a liquid, such as water, is provided to the liquid channel in order to be heated.

The liquid supply channel, also referred to as liquid channel, supplies water to the liquid chamber that may encompass the heater chamber.

In other embodiments the body further comprises at least one liquid passage between the liquid channel and the liquid chamber delimited by the hydrophobic membrane.

In other embodiments the housing further comprises at least one inlet of the liquid chamber between the liquid channel and the hydrophobic membrane.

The liquid heated by the heater flows through the liquid channel and reaches an outlet of the liquid channel, i.e. a liquid passage between the liquid channel and the hydrophobic membrane. An inlet of the liquid chamber in the housing corresponds to the outlet of the liquid channel in the body allowing the warmed liquid in the liquid channel to flow into the liquid chamber and vaporize, thereby crossing the hydrophobic liquid membrane.

Alternatively the outlet of the liquid channel may be comprised in the housing.

It may also be that the inlet of the liquid chamber is comprised in the body.

In some embodiments the body is substantially cylindrical and the at least one inlet of the liquid chamber is disposed substantially annularly around the liquid channel.

In some further embodiments the heater is placed coaxially to the body and the liquid chamber is disposed substantially annularly around the heater.

In some embodiments the hydrophobic membrane is disposed substantially annularly around the body.

In further embodiments the liquid chamber encompasses the heater.

Other locations of the liquid chamber in relation to the heater are possible. In general the heater is configured to heat the liquid chamber, i.e. to heat the liquid contained into the liquid chamber, thus locations of the heater and the liquid chamber are so as to allow for direct or indirect contact between the heater and the liquid chamber. The heater may be in direct contact with the liquid contained in the liquid chamber. The heater may be in indirect contact with the liquid chamber by being in contact with elements that allow for heat transfer to the liquid chamber and in turn to the liquid therein contained.

In some embodiments the humidifier further comprises at least one fluid passage.

The fluid may be air, thus the fluid passage may be an air passage. The humidifier humidifies the air flowing outside the housing, i.e. at the surface of the hydrophobic membrane. In order to direct and guide the air towards the area where vapour from the hydrophobic membrane is released, a fluid passage may be present. Thus, when the humidifier is inserted into a respiratory tube or into a connector between a respiratory tube and the outlet of a ventilator, it directs the air flow originated at the outlet of the ventilator towards the respiratory tube through the area where vapour from the hydrophobic membrane is released.

Thus, in some further embodiments the least one fluid passage is configured to allow fluid to flow externally to the hydrophobic membrane permeable to the vapour phase of the liquid.

In some embodiments at least one fluid passage is disposed substantially annularly around at least one part of the body.

The body may be described as comprising a first part and a second part, the first part comprising the at least one fluid passage. When the body is place in the housing, the second part lies inside the housing, while the first part lies outside the housing.

In some embodiments the first part, comprising the at least one fluid passage has a cross section diameter larger than the cross section diameter of the housing.

Generally the function of the fluid passage is to direct and allow for air flow towards the area where the air is humidified and to hold the humidifier in the centre of the respiratory tube allowing for air flow with minimum restrictions. Thus, the fluid passage may be a single annular tube surrounding the heater. The fluid passage may also be multiple channels radiating from the centre of the body, thus having a spoke like fashion cross section, thereby allowing for minimum resistance to the air flow. The fluid passage may also have a size up to the diameter of the connector or respiratory tube in which the humidifier may be contained.

In some embodiments the humidifier has dimensions allowing it to be contained in a standard respiratory tube. The humidifier is compact and lightweight and can be fully integrated into a respiratory tube or contained in a connector having size of the order of magnitude of the respiratory tube.

The size of the humidifier has great advantages, e.g. it adds minimal compliance, resistance and dead-space in the patient circuit.

Further the reduced size allows for placing of the humidifier in the inspiratory limb, or to integrate it with the ventilator at the outlet port.

For example the size of the humidifier may be in the range between 30 and 180 mm, such as between 50 and 150 mm, preferably between 60 and 130 mm, even more preferably between 75 and 120 mm. The diameter of the humidifier may be smaller than 50 mm, such as in the range between 40 and 5 mm, preferably smaller than 30 mm, such as in the range between 20 and 10 mm. For example the cross section of the humidifier may have a diameter of 12 mm.

The size of the humidifier allows also for a faster response rate as a larger heating surface heats a small volume of water providing faster evaporation.

The described objects and several other objects are intended to be obtained in a third aspect of the invention by providing a respiratory tube comprising a humidifier according to the first aspect of the invention.

The described objects and several other objects are intended to be obtained in a fourth aspect of the invention by providing a ventilation system comprising: a ventilator; a patient circuit comprising an expiration tube and an inspiratory tube, wherein the inspiratory tube comprises a humidifier according to first aspect of the invention.

The humidifier comprising the body and the housing may be inserted into the inspiratory tube or into a connector that is coupled to the outlet of the ventilator on one side and to the inspiratory tube on the other side allowing for humidification of the air passing through the connector or through the inspiratory tube.

The humidifier can be coupled to the ventilator in in any orientation, i.e. 360° at the ventilator outlet port.

The described objects and several other objects are intended to be obtained in a fifth aspect of the invention by providing a disposable housing for a humidifier for use in a patient ventilation circuit, the disposable housing comprising: an inlet, configured to receive a body comprising a heater and a liquid channel; an outlet allowing for release of vapour provided by said body; a compartment located between the inlet and outlet, for housing the body; a hydrophobic vapour permeable membrane located at least onto the outlet, thereby allowing vapour to be released externally to the housing.

The use of a disposable housing has the advantage of avoiding bacterial contamination as membrane and housing are disposed after each use.

The body, i.e. the aluminium core containing the heater, the temperature sensor and the liquid channel is re-useable and can be sterilized, e.g. in autoclave.

In some further embodiments the disposable housing according to the fifth aspect, further comprises fastening means to fasten the housing to the body.

The hydrophobic vapour permeable membrane may be fasten to the housing by fastening means such as crimps.

The invention further relates to a method to humidify air at the outlet of a ventilator, the method comprising inserting a humidifier according to the first aspect of the invention into a connector; placing the connector between the outlet of a ventilator and a respiratory tube, operating the humidifier while air is blown by the ventilator, thereby providing humidified air at the end of the respiratory tube, i.e. at the proximal part of the respiratory tube.

The main idea of the invention is a humidifier for use in a patient ventilation circuit comprising a heater for heating water and a hydrophobic vapour permeable membrane surrounding the heater in contact with the water, thereby allowing the vapour produced by heating the water to pass through the membrane, while water in the liquid form is blocked at the surface of the membrane.

The first, second, third and other aspects and embodiments of the present invention may each be combined with any of the other aspects and embodiments. These and other aspects of the invention will be apparent from and elucidated with reference to the embodiments described hereinafter.

BRIEF DESCRIPTION OF THE FIGURES

The humidifier according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
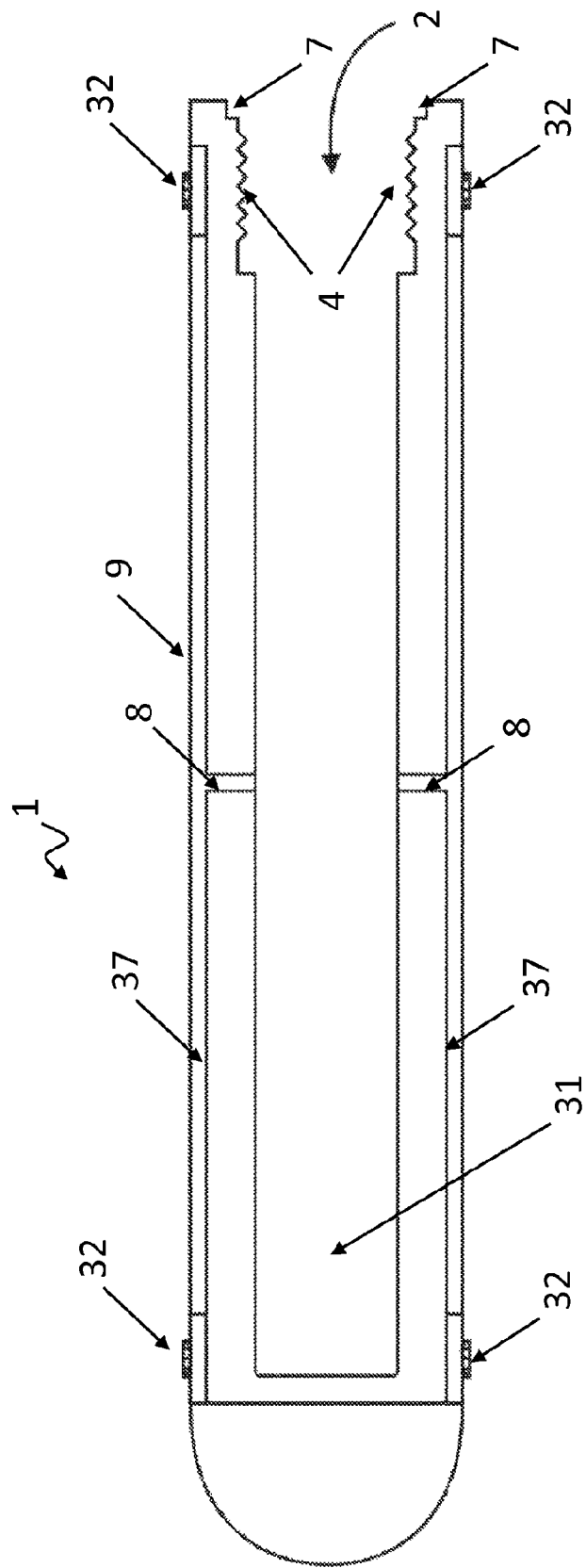
FIG. 1 is a simplified cross-sectional view of a part of a humidifier according to one aspect of the invention.

FIG. 1 is a simplified cross-sectional view of a housing, also referred to as a cartridge, for the core of the humidifier according to one aspect of the invention.

Figure 2:
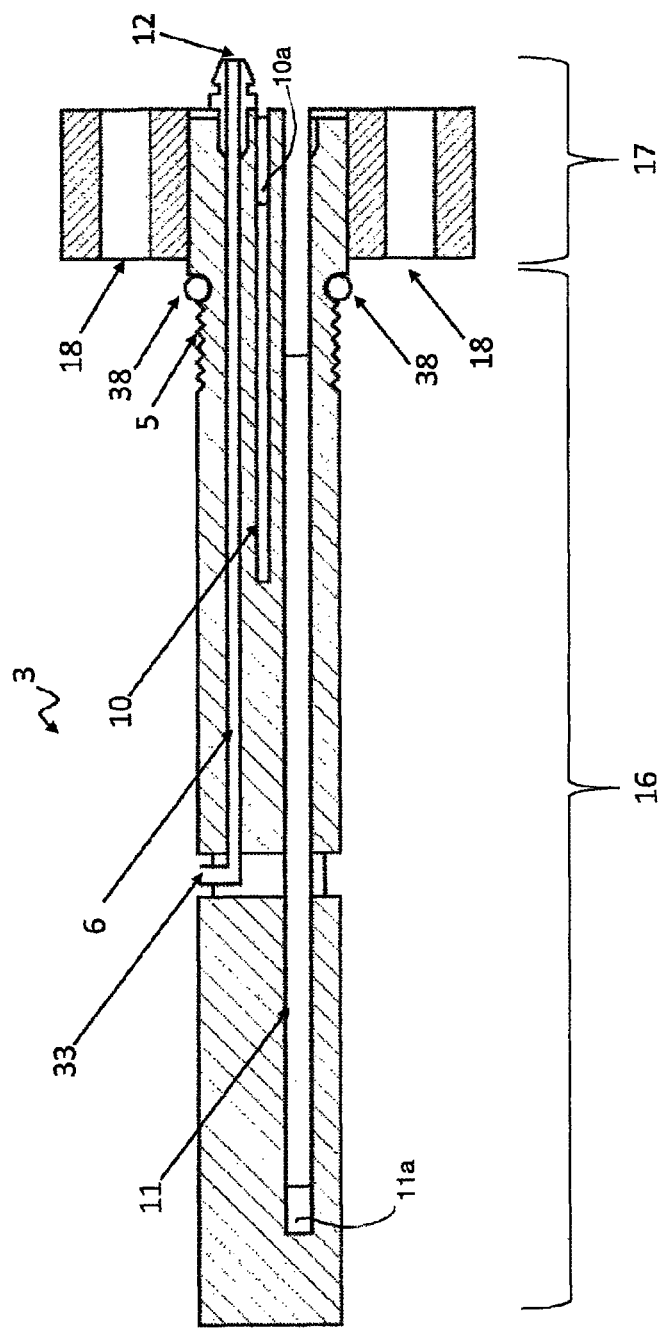
FIG. 2 is a simplified cross-sectional view of another part of a humidifier according to some embodiments of the invention.

FIG. 1 shows a disposable housing 1 for a humidifier for use in a patient ventilation circuit comprising an inlet 2 configured to receive a body 3. The inlet 2 is an opening in the housing 1 allowing for insertion of a body. The inlet 2 may comprise fastening means 4 designed to mate with a complementary fastening means 5 onto the body 3 as shown in FIG. 2. For example, a helical ridge wrapped around the body 3, i.e. an external thread 5 on body 3 may be used complementary to an internal thread 4 on internal surface of the inlet 2.

Fastening means 4 insure fastening of the body to the housing. To avoid eventual leakage of the liquid, such as water, introduced via liquid channel 6 of body 3, areas 7 are present on the inlet 2 complementary to o-ring seal 38 on body 3.

Fastening means 4 as shown in FIG. 1 and complementary fastening means 5 as shown in FIG. 2 are represented in a nut and bolt fashion. However, other fastening means may be used employing different mechanisms such as interference fit, or press-fit between parts on the housing 1 and on the body 3.

The housing 1 comprises at least one inlet 8 allowing for liquid entering the liquid chamber 37. When in use, the liquid introduced via liquid inlet 12 flows through liquid channel 6 of body 3 reaching the liquid passage or outlet 33 corresponding to the inlet 8 of the liquid chamber 37 in the housing 1. The hydrophobic membrane 9 is hydrophobic, i.e. water, introduced via liquid channel 6 of body 3 and present in the liquid chamber 37, due to intermolecular interactions does not maintain contact with the membrane. The hydrophobic membrane 9 is permeable to vapour, i.e. the vapour produced by heating the liquid in the liquid chamber 37 and liquid channel 6 getting in contact with membrane 9 crosses the membrane, while liquid is not able to pass.

The housing 1 comprises also means for fastening the hydrophobic membrane 9 to the external surface of the housing, such as crimps 32.

The housing 1 is disposable as after use may be removed by, e.g. unscrewing it from its core, i.e. the body 3 and replaced with a new housing.

The body 3 may be reused and it may be easily sterilised, e.g. in an autoclave.

FIG. 2 is a simplified cross-sectional view of the core, i.e. body 3, of a humidifier according to some embodiments of the invention.

The core, i.e. body 3, of the humidifier comprises a liquid, such as water, supply channel 6, a temperature sensor chamber 10a and a heater chamber 11a.

Liquid, such as water flows into the water supply channel 6 through a water supply port 12 which can be connected via tubing or can be snapped directly to a water bottle or a water canister. Optionally the supply of water to the water channel 6 and in turn to the water chamber 37 can be controlled through the presence of a leak sensor probe detecting water leak in any orientation. In this way the water supply to the humidifier can be easily shut down if needed.

The temperature sensor chamber 10a accommodates a temperature sensor 10, such as a thermocouple for temperature control of the humidifier.

The heater chamber 11a accommodates a heater element 11. The temperature sensor may sense the temperature of the heater element inside the heater chamber and eventually control its temperature though a control unit (not shown).

The body 3 may be made of metal, such as a heat conductive metal. For example body 3 may be made of aluminium or aluminium alloys. Thus, heater element, temperature sensor and water supply channel 6 are enclosed into a shell of conductive metal.

The body 3 comprises also a fastening mean complementary to the one in the housing, e.g. an external thread 5 complementary to internal thread 4 on the intern surface of the housing 1.

The body 3 may further comprise o-ring seal 38 that when the housing is sealed with the body to ensure from eventual liquid leakage.

Figure 3:
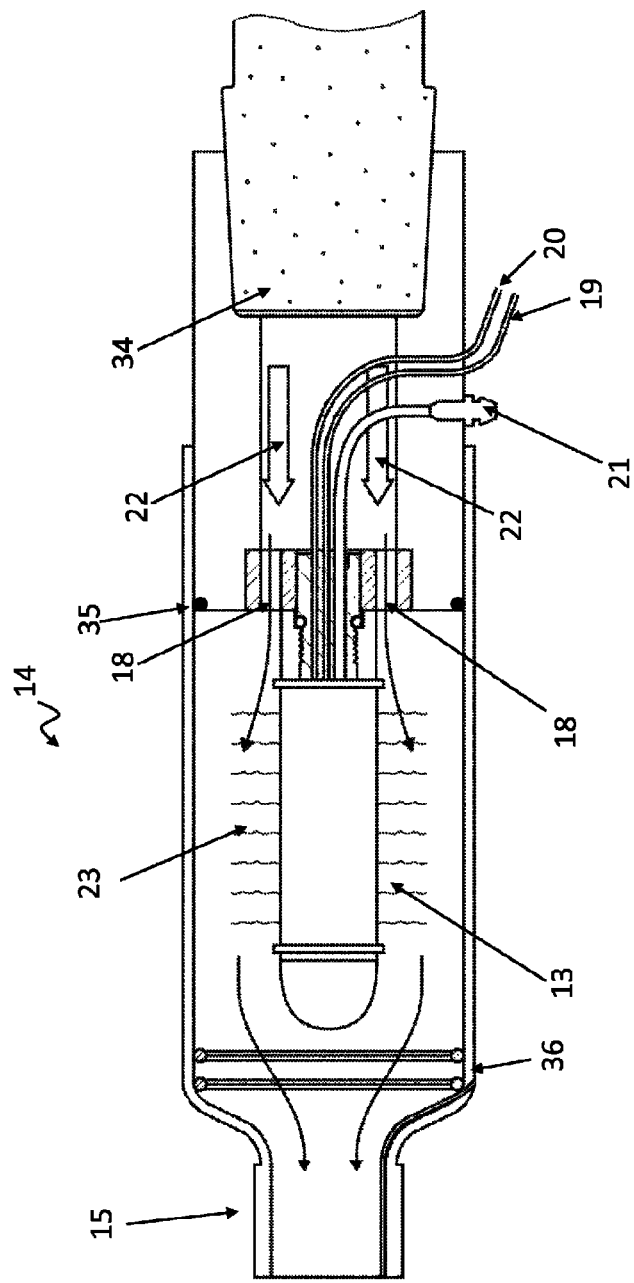
FIG. 3 is a simplified cross-sectional view of a respiratory tube including a humidifier according to some embodiments of the invention.

The body 3 may comprise a first part 17 and a second part 16. When the body is placed into the housing the second part 16 lies completely inside a body receiving chamber 31 of the housing 1, while the first part 17 lies outside the housing 1. The first part 17 may comprise at least one passage 18 allowing the flow 22 of the air from the outlet 34 of a ventilator to reach the area 23 where the air is humidified and heated before entering the respiratory tube 15, as shown in FIG. 3. Passage 18 may be disposed substantially annularly around body 3 as shown in FIG. 2. In some other embodiments the passage 18 may be placed differently. Generally the passage is adapted to allow air flow towards area 23 and/or in contact with the external surface of the membrane 9 of housing 1.

In some embodiments the fluid passage is not comprised in the body 3.

In FIGS. 2 and 3 the passage 18 is represented having a specific diameter. However, the diameter of the fluid passage may vary, e.g. up to the diameter of the connector or respiratory tube in which the humidifier is contained. The passage 18 is designed so as to allow for air flow with minimum restrictions. Thus optimization of dimension and shape of the passage may be achieved and implemented by means of computer simulation and/or experimentation directed towards minimization of air flow restrictions.

FIG. 3 is a simplified cross-sectional view of a respiratory tube including a humidifier according to the embodiment of the invention.

A humidifier 13 comprising a core 3 and a housing 1 as shown in FIG. 3 is located inside a connector 14 connecting the outlet 34 of a ventilator (not shown) with a respiratory tube 15, such as an inspiratory tube.

The humidifier 13 is placed coaxially inside the connector 14. However in other embodiments the humidifier 13 may be place differently to further minimize resistance in the respiratory tube 15 of the patient circuit.

Optionally the o-rings 35 may be used to insure tight connection between the connector 14 and the outlet 34.

Leak sensor probe 36 may be positioned inside the connector 14 to detect and avoid leakage.

FIG. 3 shows also the electrical connection 19 to the temperature sensor inside chamber 10 and electrical connection 20 to supply the heater inside chamber 11 with electricity. Water is supplied via tubing 21.

In some embodiments the humidifier 13 may be placed directly inside respiratory tube 15.

When in use, air generated via a ventilator system (not shown) reaches the respiratory tube via an outlet 34. Here air flow in the direction of arrows 22 and through passage 18 reaches area 23 of connector 14, surrounding the humidifier 13. Inside humidifier 13 the water present in chamber 10 and provided via tubing 21 is heated by the heater element located inside heater chamber 11. Heating of the liquid produces vapours that, passing through the hydrophobic, vapour permeable membrane 9 of the housing 1, are released in the area 23. The flow of air passing through area 23 gets therefore humidified and heated before entering the respiratory tube 15.

Figure 4:
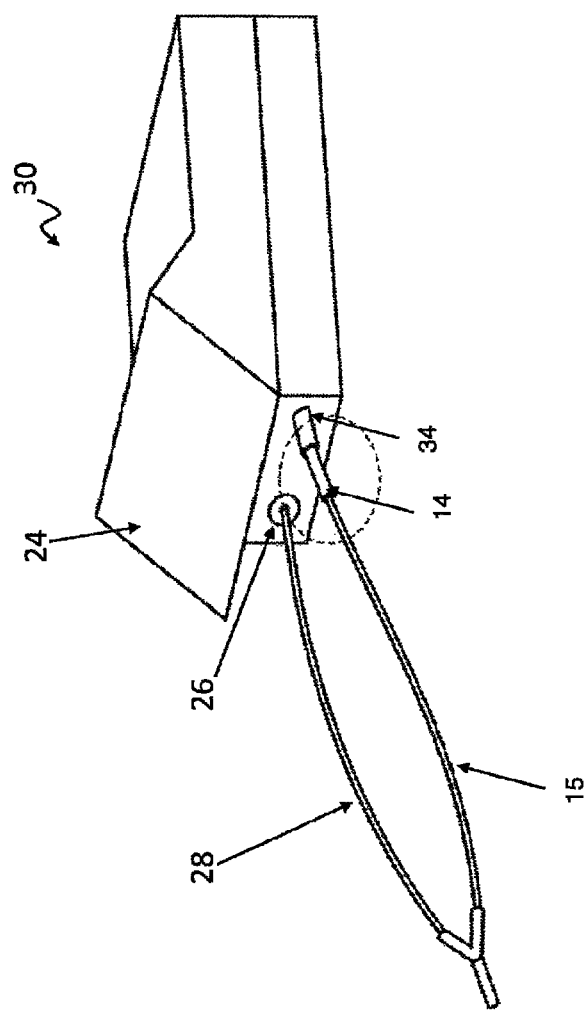
FIG. 4 is a perspective view of a ventilator system according to some embodiments of the invention.

FIG. 4 is a perspective view of a ventilator system 30 according to some embodiments of the invention. A ventilator 24 including the air outlet 34 and an air inlet 26 respectively connected to an inspiratory respiratory tube 15, also referred to as inhalation limb and an expiratory tube 28, referred to as exhalation limb. From FIG. 4 it can be noticed that due to its limited size, the humidifier in the connector 14 may be easily integrated into the inhalation limb 15 of the ventilation system 30.

The humidifier of the invention may be used for adult, paediatric and neonatal ventilation therapies that require heated humidification of gases for home or hospital use. This humidifier may also have applicability to other gas humidification products.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A humidifier for use in a patient ventilation circuit, said humidifier comprising:
   a heater configured to heat a liquid,
   a hydrophobic membrane permeable to a vapor phase of said liquid, wherein said heater configured to heat said liquid is surrounded by said hydrophobic membrane permeable to the vapor phase of said liquid, thereby allowing for crossing of said membrane only by the vapor phase of said liquid,
   wherein said heater configured to heat the liquid is disposed in a re-useable humidifier body and said hydrophobic membrane permeable to the vapor phase of said liquid is located on an external surface of a disposable humidifier housing configured to be disposed over said humidifier body,
   wherein said humidifier housing further comprises at least one inlet of a liquid chamber between a liquid channel and said hydrophobic membrane, and
   wherein said humidifier body is substantially cylindrical and said at least one inlet of said liquid chamber is disposed substantially annularly around said liquid channel.

2. The humidifier according to claim 1 further comprising a temperature sensor for sensing the temperature of said heater.

3. The humidifier according to claim 1, wherein said liquid chamber encompasses said heater.

4. The humidifier according to claim 1, wherein said heater is placed coaxially to said humidifier body and said liquid chamber is disposed substantially annularly around said heater.

5. The humidifier according to claim 1, wherein said hydrophobic membrane is disposed substantially annularly around said humidifier body.

6. The humidifier according to claim 1, further comprising at least one fluid passage.

7. The humidifier according to claim 1, said humidifier having dimensions allowing to be contained in a respiratory tube.

8. A ventilation system comprising:
   a ventilator;
   a patient circuit comprising an expiration tube and an inspiratory tube, said inspiratory tube comprising the humidifier according to claim 1.

9. A humidifier for use in a patient ventilation circuit, the humidifier comprising:
   a re-usable elongated humidifier body of a heat conductive material;
   a liquid channel defined through an interior of the re-usable elongated humidifier body from an inlet to an outlet configured to discharge liquid received from the channel around a periphery of the re-usable elongated humidifier body;
   a heater disposed in the re-usable elongated humidifier body;
   a part disposed peripherally around the re-usable elongated humidifier body defining at least one air passage for directing air along the periphery of the re-usable elongated humidifier body; and
   a disposable humidifier housing including:
      a hydrophobic membrane permeable to a vapor phase of the liquid and impermeable to the liquid, the hydrophobic membrane being disposed surrounding the re-usable elongated humidifier body to define a generally annular liquid chamber peripherally around the re-usable elongated humidifier body and adjacent the hydrophobic membrane; and
      complementary fastening means on the disposable humidifier housing and the re-usable elongated humidifier body configured to permit the disposable humidifier housing to be detached from the re-usable elongated humidifier body for disposal and replacement.

10. The humidifier according to claim 9, wherein the outlet extends substantially annularly around the re-usable elongated humidifier body to deliver the liquid to the annular liquid chamber.

11. The humidifier according to claim 10, wherein the re-usable elongated humidifier body, the annular liquid chamber, and the permeable membrane are disposed coaxially.

12. The humidifier according to claim 10, wherein the at least one air passage is configured to deliver the air peripherally around the hydrophobic membrane.

13. A disposable housing for use in a humidifier including a re-usable elongated humidifier body of a heat conductive material, a liquid channel defined through an interior of the re-usable elongated humidifier body from an inlet to an outlet configured to discharge liquid received from the channel annularly around a periphery of the re-usable elongated humidifier body, and a heater disposed in the re-usable elongated humidifier body, the disposable humidifier housing including:
   a hydrophobic membrane permeable to a vapor phase of the liquid and impermeable to the liquid, the hydrophobic membrane being disposed surrounding the usable elongated humidifier body to define a generally annular liquid chamber peripherally around the re-usable elongated humidifier body and adjacent the hydrophobic membrane; and
   fastening means on the disposable humidifier housing configured to permit the disposable humidifier housing to be detached from the re-usable elongated humidifier body for disposal and a replacement housing to be attached to the re-usable elongated humidifier body.

* * * * *